United States Patent
Hacker et al.

(10) Patent No.: US 7,993,360 B2
(45) Date of Patent: Aug. 9, 2011

(54) ROTARY SHAVER WITH IMPROVED CONNECTION BETWEEN FLEXIBLE AND RIGID ROTATABLE TUBES

(75) Inventors: Randall Lee Hacker, Naples, FL (US); Robert A. Van Wyk, Largo, FL (US); Gary R. Heisler, Middleton, CT (US)

(73) Assignee: Arthrex, Inc., Naples, FL (US)

( * ) Notice: Subject to any disclaimer, the term of this patent is extended or adjusted under 35 U.S.C. 154(b) by 413 days.

(21) Appl. No.: 11/484,216

(22) Filed: Jul. 11, 2006

(65) Prior Publication Data

US 2008/0071303 A1    Mar. 20, 2008

(51) Int. Cl.
*A61B 17/32*    (2006.01)

(52) U.S. Cl. .......................................... 606/180; 606/82

(58) Field of Classification Search .............. 285/33–34, 285/139.3, 258, 323; 408/81–83; 600/36, 600/562, 564–565, 567; 606/79–82, 84, 606/110, 127, 159, 161, 167–171, 177–179, 606/180
See application file for complete search history.

(56) References Cited

U.S. PATENT DOCUMENTS

| | | | | |
|---|---|---|---|---|
| 3,430,993 A * | 3/1969 | Leshinsky | ........................ | 287/53 |
| 4,187,135 A * | 2/1980 | Yates et al. | ..................... | 156/187 |
| 4,747,406 A * | 5/1988 | Nash | ............................... | 606/159 |
| 5,156,206 A * | 10/1992 | Cox | ................................ | 285/323 |
| 5,286,253 A * | 2/1994 | Fucci | ............................... | 604/22 |
| 5,297,819 A * | 3/1994 | Harder | ............................ | 285/93 |
| 5,411,514 A | 5/1995 | Fucci et al. | | |
| 5,437,630 A | 8/1995 | Daniel et al. | | |
| 5,540,708 A * | 7/1996 | Lim et al. | ....................... | 606/170 |
| 5,922,003 A * | 7/1999 | Anctil et al. | .................... | 606/170 |
| 5,961,532 A | 10/1999 | Finley et al. | | |
| 5,967,568 A * | 10/1999 | Bird | ................................ | 285/258 |
| 6,290,438 B1 * | 9/2001 | Papajewski | .................... | 408/145 |
| 6,533,749 B1 | 3/2003 | Mitusina et al. | | |
| 6,620,180 B1 * | 9/2003 | Bays et al. | ...................... | 606/171 |
| 2004/0181250 A1 * | 9/2004 | Adams et al. | ................. | 606/170 |
| 2004/0218968 A1 * | 11/2004 | Beaver et al. | .................... | 403/95 |
| 2005/0159767 A1 * | 7/2005 | Adams et al. | ................. | 606/180 |

* cited by examiner

*Primary Examiner* — Anhtuan Nguyen
*Assistant Examiner* — Ashley Cronin
(74) *Attorney, Agent, or Firm* — Akerman Sentefitt; Michael K. Dixon

(57) ABSTRACT

An rotary shaver having an attachment device for coupling a flexible transmission shaft to rigid ends. In at least one embodiment, the rotary shaver may be a curved rotary shaver. The inner shaft may be formed from rigid ends connected together with the flexible transmission shaft via an attachment device. The attachment device may include a collar protruding from an outer surface to penetrate an inner surface of the flexible transmission shaft. The attachment device may also include one or more grooves or protrusions for the transmission of torque.

24 Claims, 17 Drawing Sheets

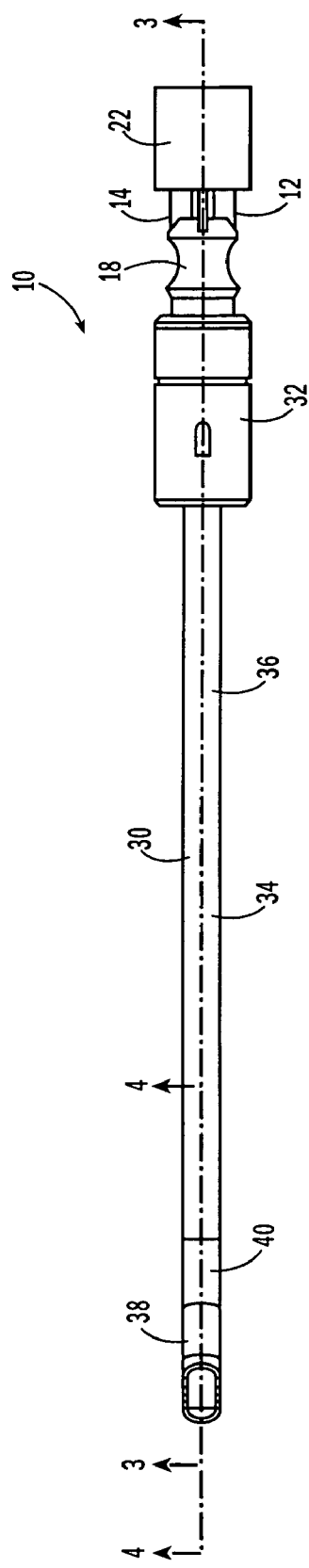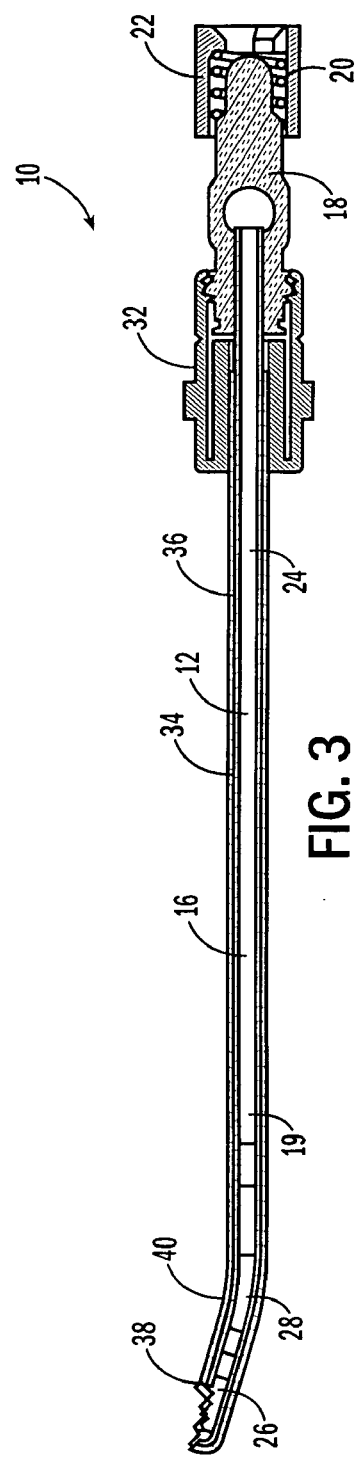
FIG. 2
FIG. 3

ROTARY SHAVER WITH IMPROVED CONNECTION BETWEEN FLEXIBLE AND RIGID ROTATABLE TUBES

FIELD OF THE INVENTION

The invention relates to rotary surgical instruments for use in endoscopic tissue resection. More particularly, the invention relates to rotary shavers having an elongated inner tube rotatably situated within an elongated stationary outer tube, whereby both inner and outer tubes have cutting apertures at their distal ends.

BACKGROUND OF THE INVENTION

The use of elongated surgical cutting instruments has become well accepted in performing dosed surgery such as arthroscopic or, more generally, endoscopic surgery. In dosed surgery, access to the surgical site is gained via one or more portals, and instruments used in the surgical procedure must be elongated to permit the distal ends of the instruments to reach the surgical site. Surgical cutting instruments for use in closed surgery—also known as "shavers"—have an elongated outer tubular member terminating at a distal end having an opening in the end or side wall (or both) to form a cutting window and an elongated inner tubular member concentrically disposed in the outer tubular member and having a distal end disposed adjacent the opening in the distal end of the outer tubular member. The distal end of the inner tubular member has a surface or edge for engaging tissue via the opening in the outer tubular member and cooperates with the opening to shear, cut or trim tissue. The inner tubular member is rotatably driven about its axis from its proximal end by a handpiece having a small electric motor which is controlled by finger actuated switches on the handpiece, a foot switch or switches on a console supplying power to the handpiece. The distal end of the inner tubular member cart have various configurations depending upon the surgical procedure to be performed, and the opening in the distal end of the outer tubular member has a configuration to cooperate with the particular configuration of the distal end of the inner tubular member. These various configurations are referred to generically as shaver blades. Cut tissue is aspirated through the hollow lumen of the inner tubular member to be collected via a vacuum tube communicating with the handpiece.

Resection of tissue by a shaver blade is accomplished by cooperative interaction between the edges of the inner and outer cutting windows. As the inner and outer windows come into alignment, the tissue is sucked into the lumen of the inner tube with a vacuum. Continued rotation of the inner member causes the inner cutting edges to approach the outer cutting edges. Tissue in the cutting window between the inner and outer edges is either trapped between the edges or ejected from the window. Tissue trapped between the edges is either cut by the edges as they approach each other or torn by the cutting edges as they pass and rotate away from each other. The resected tissue is aspirated from the site through the inner lumen of the inner tube.

Angled shaver blades, which are shaver blades having an outer tube in which a distal portion is angularly offset from a proximal portion, increase the ease with which a surgeon is able to access certain tissues and locations within the surgical field. Curved shavers are well known in the art, such as shown in U.S. Pat. No. 5,437,630 to Daniel et al, U.S. Pat. No. 5,411,514 to Fucci et al, and U.S. Pat. No. 5,961,532 to Finley et al. In general, angled shavers have an outer tubular member with a linear proximal portion and a linear distal portion joined by a curved portion such that the distal portion is angularly offset from the proximal portion. The rotatable inner member is an assembly which has a rigid linear proximal portion, and a rigid linear distal portion having a distal end configured for cutting or abrading tissue. A flexible portion couples the distal end of the proximal linear portion and the proximal end of the linear distal portion together.

Angled shavers may be divided into two categories according to the construction of the flexible portion of the rotatable inner member. The first category includes shavers having flexible portions formed of couplings made of metallic materials. Such couplings are made of one or more layers of helically formed sheet or springs. The coupling may be formed from multi-layer couplings having the helixes or coils of adjacent layers formed in opposite directions, i.e. a right-hand helix adjacent to a left-hand helix, so as to increase the torsional strength of the coupler. Such construction is disclosed by U.S. Pat. No. 5,411,514 to Fucci et al., U.S. Pat. No. 6,533,749 to Mitusina et al., and by others.

The second category includes angled shavers in which the flexible portion of the rotating inner member is made of a polymeric material. Such construction is disclosed by U.S. Pat. No. 5,961,532 to Finley et al., U.S. Pat. No. 5,540,708 to Fucci et al., U.S. Pat. No. 5,922,003 to Anctil et al., U.S. Pat. No. 6,620,180 to Bays et al. and others. The simplified construction of a shaver with polymeric flexible portions results in decreased manufacturing costs.

During use, tissue occasionally lodges in the lumen of the distal portion of the Inner tubular member. These "clogs" prevent effective use of the instrument and must be removed by the surgeon so that the operation can continue. To remove a clog, the instrument is withdrawn from the joint. The inner tubular member is removed from the outer member and a wire or other declogging device inserted into the distal end of the inner member to dislodge the tissue obstructing the lumen. It is essential that a shaver blade be constructed in a manner which allows the inner drive assembly to be easily removed from the outer housing. In the case of angled shavers, removal of the inner drive assembly is complicated because the straight distal portion of the inner drive assembly must pass through the curved portion of the outer tube. Because of this complication, the diameter of the distal linear portion of the inner drive assembly is less than the diameter of the lumen of the curved portion of the outer tube to facilitate easy withdrawal. However, even with this configuration, significant proximal axial force must be applied to the proximal end of the inner drive assembly to withdraw the inner drive assembly from the outer housing. The withdrawal resistance is generally greater for inner assemblies with polymeric flexible portions, especially those having flexible portions made from homogeneous high-strength polymers such as PEEK (polyetheretherketone). The rigidity of these polymeric materials creates high frictional forces between the flexible portion of the inner drive assembly and the curved portion of the outer housing. The rigidity of these materials also creates high frictional forces between the rigid distal portion of the inner drive assembly and the curved portion of the outer tube, and between the rigid distal portion of the inner drive assembly, and the linear distal portion of the outer housing during the initial portion of withdrawal. The axial forces on the rigid distal portion of the inner drive assembly may dislodge the inner drive assembly from the distal end of the flexible portion. The forces also tend to cause failure of the assembly at the juncture between the distal end of the proximal rigid portion of the inner drive assembly and the proximal end of the flexible portion. In view of these potential failures, the attachment of the polymeric portion to the rigid portions of the inner drive assembly must be capable of transmitting torsional forces to effect the cutting or abrading of tissue and preventing failure of the inner drive assembly during disassembly.

There exist various methods of attachment. For instance, U.S. Pat. No. 5,540,708 to Lim et al. discloses use of laterally opposed protrusions on the proximal end of the inner drive and mating grooves in the distal end of the flexible portion of the inner drive assembly to transmit torque to the drive. Barbs are included on the proximal end of the protrusions penetrate the side walls of the slots in the polymeric portion so as to retain the drive on the polymeric portion when the drive is subjected to axial tensile forces. This method of attachment is expensive because machining is required to create the slots in the polymeric material and corresponding protrusions on the inner drive. Also, the strength of the joint when subjected to axial forces is relatively weak because the drive is retained to the polymeric portion only by four small barb portions which embed themselves in the slot walls of the polymeric portion. Because of manufacturing tolerances and the resulting variations in component features sizes, the amount of penetration of the barb portions into the walls of the polymeric tube slots will vary significantly with resulting variation in the retention strength.

U.S. Pat. No. 5,922,003 to Anctil et al. discloses an inner drive having a proximal portion with a reduced diameter having various holes or elongated slots of various configurations. The slots extend between the inner and outer cylindrical surfaces of the reduced portion. The proximal portion of the drive, which is slightly larger in diameter than the lumen of the tubular portion, is assembled into the distal end of the polymeric tubular portion. The joint is heated to a temperature at which the polymeric material in the overlapping region flows into the holes and passages of the drive proximal region so as to form a mechanical bond having torsional and tensile strength. The device taught by Anctil et al. uses a polymeric material having a low melting point and relatively low strength and rigidity. The necessary strength and rigidity are achieved through a wire mesh that is embedded in the polymeric portion. This bonding method cannot be used with higher rigidity, higher strength materials such as PEEK.

U.S. Pat. No. 5,961,532 to Finley et al. discloses a method of attachment in which a tubular flexible transition shaft has a lumen of varying diameters. Specifically, the lumen has regions of increased diameter at its proximal and distal ends to form "annular flanges". The proximal portion of the inner drive and the distal portion of the proximal rigid portion of the inner drive assembly have reduced diameters and are textured with "hills and valleys". The distal and proximal portions of the lumen of the flexible transition shaft with larger diameters have "complementary hills 65 that seat in the valleys of annular flange 62". The mechanical interlocking of the complementary features enables the joints to transmit torque and provides tensile strength. However, the process of forming the complementary features on the inner lumen portions and annular flanges is problematic because the walls of the tubular segments are quite thin and forming such features causes the walls to deform.

Thus, there is a need for an improved connection for joining a polymeric flexible portion of a shaver blade inner drive assembly to a rigid distal tip and to the flexible transmission shaft of the assembly. In addition, there is a need for an improved connection that is easy to produce and provides high torsional and axial strength when used with high-strength polymeric materials, such as PEEK.

SUMMARY OF THE INVENTION

This invention is directed to an inner drive assembly for an angled endoscopic shaver having an improved connection system for connecting a flexible transmission shaft to a rigid drive shaft and to a rigid distal tip. The flexible transmission shaft enables the inner drive assembly to be used with an outer housing that is angled or bent. The flexible transmission shaft enables the rigid distal tip to the inserted into and withdrawn from the angled outer housing. In one embodiment, the flexible transmission shaft may be formed from a flexible material, such as, but not limited to, a high-strength polymeric material, such as PEEK. The rotary shaver may be formed from a rigid distal tip having a plurality of teeth positioned proximate to a distal opening for cutting tissue, an opening at a proximate end of the rigid distal tip, and a flexible shaft connection device at the proximate end. The rotary shaver may also include a rigid drive member having a drive attachment device at one end and a flexible shaft connection device at another end. A flexible transmission shaft may be coupled to the rigid distal tip at the flexible shaft connection device of the rigid, distal head and may extend from the rigid, distal head to the rigid drive member and may be attached to the flexible shaft connection device of the rigid drive member. The flexible transmission shaft may be coupled to the rigid distal tip and the rigid drive member with an interference fit. In particular, the distal end of the rigid proximal portion and the proximal end of the rigid distal portion of the inner drive assembly may have a reduced diameter slightly greater than the diameter of the lumen of the polymeric portion.

The flexible shaft connection device of the rigid distal tip and of the rigid drive member may include at least one collar protruding from an outer surface and positioned between a stop and an end of the flexible shaft connection device to attach the flexible transmission shaft. The collar may be positioned generally orthogonal to a longitudinal axis of one of the flexible shaft connection device of the rigid distal tip and of the rigid drive member. The rotary shaver may also include one or more grooves positioned in the outer surface and positioned generally along a longitudinal axis of the flexible shaft connection device of the rigid distal tip and or the rigid drive member from which the at least one collar extends. The rotary shaver, in at least one embodiment, may include a plurality of grooves extending generally along a longitudinal axis. The groove may include first and second sides extending from the outer surface and intersecting one another. The groove may extend from an end of the flexible shaft connection device toward the stop and may terminate between the collar and the stop. A depth of the groove on a first side may be greater than a depth of the groove on a second side to facilitate edges of the groove digging into or protruding into the flexible shaft connection. In another embodiment, a depth of the groove along a center line of the groove may be less than a depth of the groove at first and second sides of the groove thereby forming a torque transmitting connection device capable of transmitting torque when the flexible shaft is rotated in both clockwise and counterclockwise directions. In another embodiment, protrusions may be formed on the cylindrical surface without grooves. In yet another embodiment, the rotary shaver may include grooves and protrusions.

The rotary shaver may also include a second collar that protrudes from the outer surface and may be positioned between the first collar and the end of the flexible shaft connection device. The rotary shaver may also include a plurality of projections extending from the outer surface between the collar and the end of the flexible shaft connection device. In another embodiment, the rotary shaver may include a plurality of axial ribs positioned between the collar and the end of the flexible shaft connection device. The end may also be tapered to facilitate attachment of the flexible transmission shaft to the rigid member.

The inner drive assembly may be formed by inserting the proximal end of the rigid distal tip into the distal end of the flexible shaft such that the reduced proximal portion of the drive is within the polymeric portion. The inclined proximal surface of the collar facilitates the flexible transmission shaft sliding over the collar. Applying tension to the joint after it is formed causes portions of the collar between the grooves to engage the flexible transmission shaft to prevent separation of the joint and to transmit torque to the rigid distal tip. Because the proximal portion of the rigid distal tip and the rigid drive member is larger than the lumen of the flexible transmission shaft, portions of the flexible transmission shaft material deform into the grooves in the surface of the proximal portion of the rigid distal tip and the rigid drive member to further aid in transmitting torque to the drive. In another embodiment, the collar may function in the same manner; however, protrusions on the outer surface of the rigid distal tip and the rigid drive member proximal portion may penetrate into the flexible transmission shaft to transmit torque and increase the tensile strength of the joint.

An advantage of this invention is that the rotary shaver includes a flexible shaft connection device having improved holding ability such that forces larger than successfully handled by conventional systems may be transmitted from a rigid drive transmission to the flexible transmission shaft and from the shaft to the rigid distal tip. As a result, the rotary shaver may be used in more rigorous applications without failure.

BRIEF DESCRIPTION OF THE FIGURES

FIG. 2 is a top view of the shaver of FIG. 1 assembled for use.

FIG. 3 is a cross-sectional view of the shaver of FIG. 2 taken along line 3-3.

DETAILED DESCRIPTION OF THE FIGURES

Figure 1:
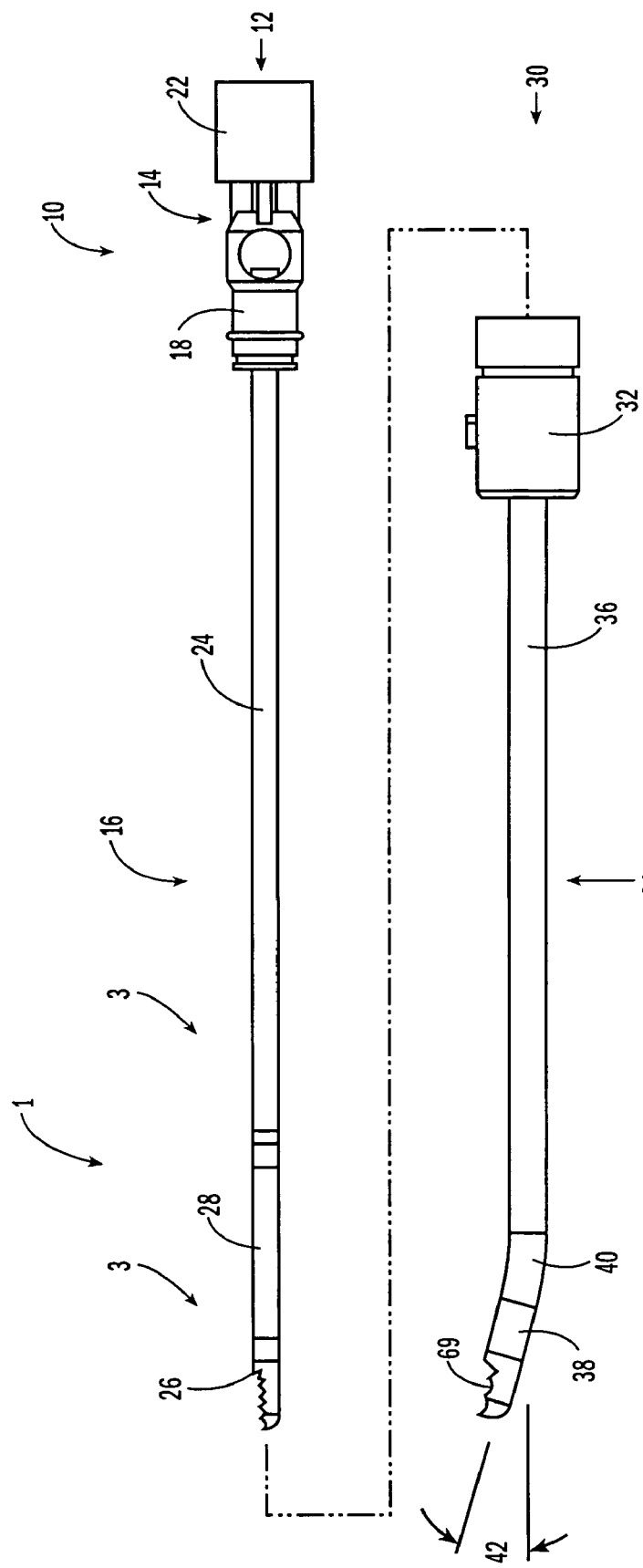
FIG. 1 is an exploded side view of an angled shaver having aspects of this invention.

As shown in FIGS. 1-26, this invention is directed to a connection system 1 configured to attach a flexible transmission shaft 28 to a rigid member 3, such as a rigid distal tip 26 or rigid proximal portion 24. The connection system 1 facilitates the transmission of torque and axial forces between the flexible transmission shaft 28 and the rigid distal tip 26 or between the flexible transmission shaft 28 and the rigid proximal portion 24. The connection system 1 may be used together with a rotary shaver 10, such as those typically used various in surgical procedures to remove tissue and bone. In at least one embodiment, the connection system 1 may be used together with a curved rotary shaver 10, as shown FIGS. 1-3.

In at least one embodiment, the angled shaver 10 may be formed from an inner drive assembly 12 and an outer housing 30. Inner drive assembly 12 may include a drive system 14 and an elongated distal portion 16. Drive system 14 may be formed from any appropriate device configured to transmit torque to the inner drive assembly 12. In one embodiment, the inner drive system may include a hub 18 and a spring 20 and a spring retainer 22 for engaging a drive device (not shown).

The elongated distal portion 16 may be formed from a rigid proximal portion 24, a rigid distal tip 26 and a flexible transmission shaft 28 extending between the rigid proximal portion 24 and the rigid distal tip 26. The flexible transmission shaft 28 may be formed from a suitable flexible material such as, but not limited to, a polymeric material, such as PEEK, or other appropriate materials. The rigid proximal portion 24 may be a shaft formed from any appropriate material, such as but not limited to, stainless steel titanium and other rigid materials. Similarly, the rigid distal tip 26 of the drive system 14 may be formed from any appropriate material, such as but not limited to, stainless steel titanium and other rigid materials. It will be understood that in the embodiments herein described, distal portion 50 of inner proximal portion 24 of the drive system 14 may be identical in configuration to proximal portions 46 of rigid distal tips 100, 200, 300, 400 and 500, and functions in the same manner.

As shown in FIG. 1, the outer housing 30 may include a hub assembly 32. An elongated rigid distal portion 34 may extend from the hub assembly 32 and may be formed from a hollow tube sized to receive the inner drive assembly 12. The distal portion 34 may include a linear proximal shaft 36, a distal linear portion 38 and a curved portion 40 such that distal portion 38 is offset from proximal portion 36 by an acute angle 42. The distal linear portion 38 may include a cutting window 69.

Figure 4:
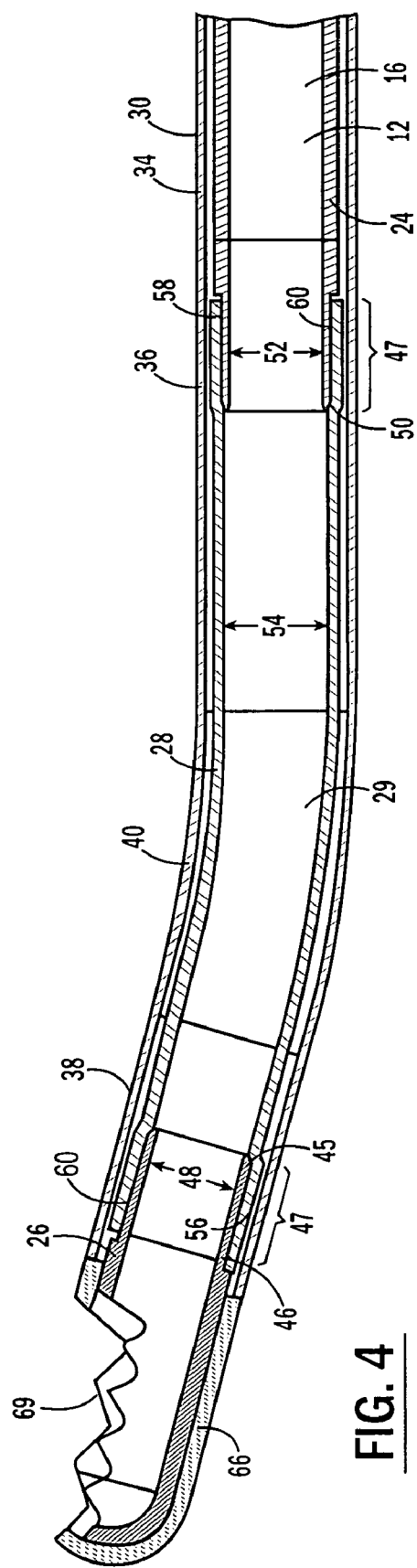
FIG. 4 is a detailed cross-sectional view of the distal portion of the shaver of FIG. 2.
Figure 5:
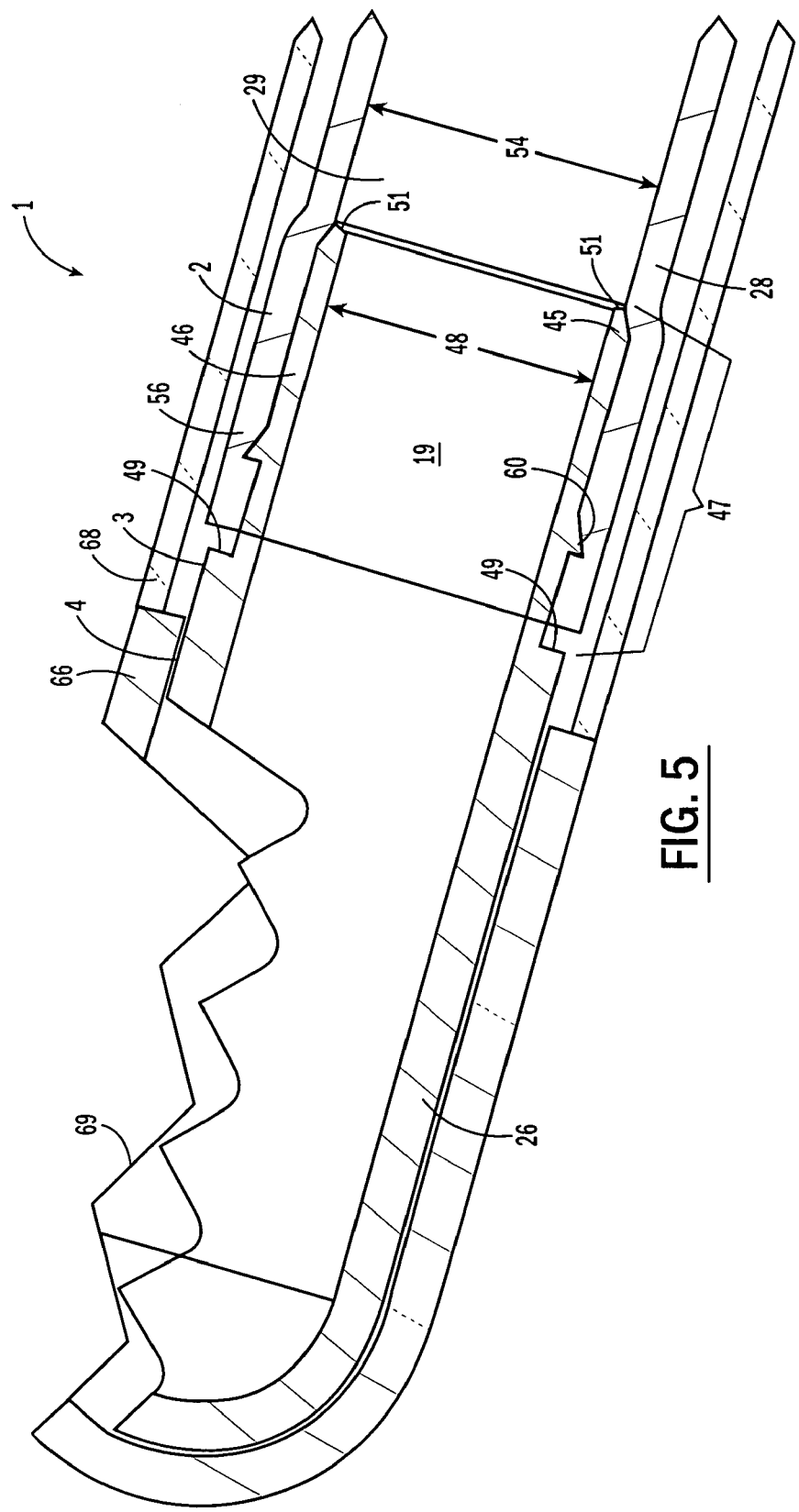
FIG. 5 is a detailed view of the distal portion of the objects shown in FIG. 4.
Figure 6:
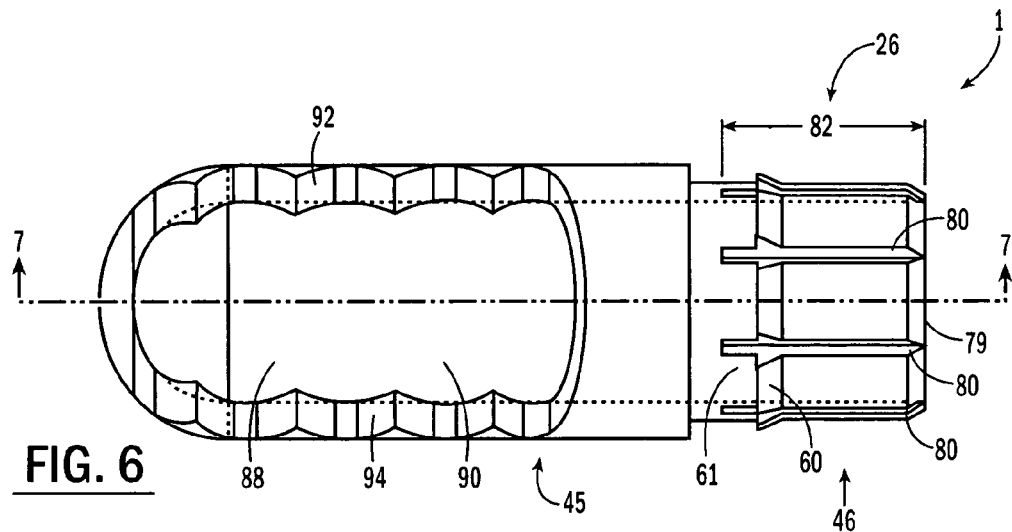
FIG. 6 is a top view of the inner rigid distal tip.
Figure 7:
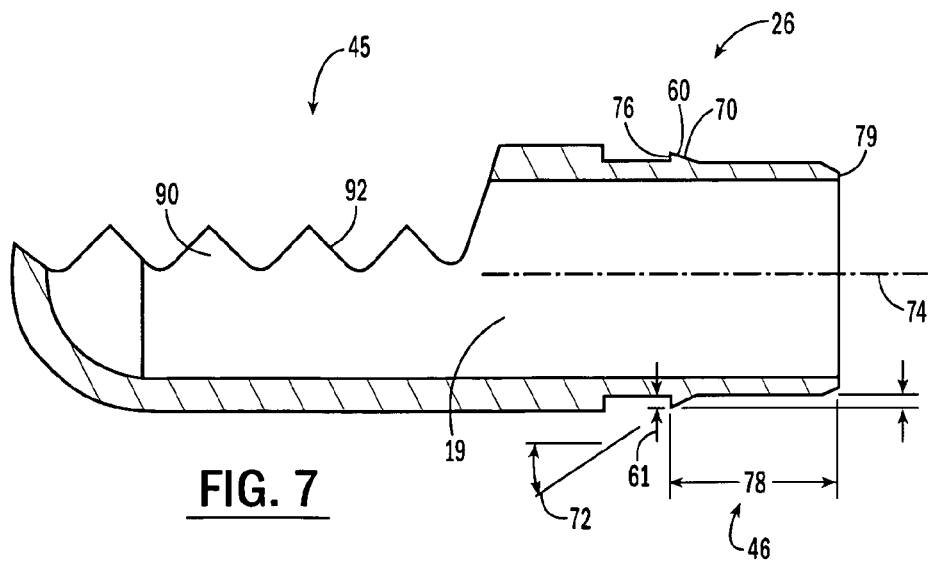
FIG. 7 is a cross-sectional view of the inner rigid distal tip of FIG. 6 taken along line 7-7.

The connection system 1 may be configured such that the rigid member 3 includes a receiver 47 having a reduced diameter relative to other portions of the rigid member 3, as shown in FIGS. 4-8, 10-17, 19, 20, 23 and 24. The receiver portion 47 may include stop 49 and end 51 defining the receiver 47. The receiver 47 may be sized such that an interference fit is formed between the receiver 47 and the flexible transmission shaft 28. In particular, as shown in FIGS. 4 and 5, rigid distal tip 26 may have a distal portion 45 and a proximal portion 46 with a diameter 48, and rigid proximal portion 24 of the drive system 14 may have a distal portion 50 with a diameter 52. In one embodiment, diameters 48 and 52 may be approximately equal. The flexible transmission shaft 28 may have a lumen 29 with a diameter 54. The diameter 54 may be slightly less than diameters 48 and 52 to create an interference fit. The receiver 47 on the proximal portion 46 of rigid distal tip 26 may be positioned in the distal end 56 of the flexible transmission shaft 28. Similarly, the receiver 47 on the distal portion 50 of proximal inner portion 24 of the drive system 14 may be positioned in the proximal end 58 of flexible transmission shaft 28. This interference fit enhances the ability of the connection system 1 to transmit axial forces and torque across the connections between the rigid and flexible transition shafts.

The connection system 1 may also include one or more flexible shaft connection devices 60 protruding from an outer surface 61 of the rigid members. The flexible shaft connection device 60 may be a device for enhancing the connection between the flexible transmission shaft 28 and the rigid member 3. In at least one embodiment, the flexible shaft connection device 60 may be a collar 60. The collar 60 may be positioned generally orthogonal to a longitudinal axis 74. In other embodiments, the collar 60 may be positioned at other angles relative to the longitudinal axis 74. The collar 60 may extend completely around the proximal portion 46 of rigid distal tip 26 and around the distal portion 50 of proximal portion 24 of the drive system 14. In other embodiments, the collar 60 may extend only partially around the proximal portion 46 of rigid distal tip 26 and partially around the distal portion 50 of proximal portion 24 of the drive system 14. The collar 60 on proximal portion 46 of rigid distal tip 26 and on distal portion 50 of proximal portion 24 of the drive system 14 may penetrate into the lumen 54 of the flexible transmission shaft 28. As shown in FIG. 5, the distal linear portion 38 of the outer housing 30 may have a distal-most portion 66 attached to a tubular portion 68. Cutting window 69 may form laterally opposed cutting edges.

As shown in FIGS. 6-9, the collar 60 on the rigid distal tip 26 may have a height 61. The height 61 may be between about 0.002 and about 0.015 inches, and more preferably between about 0.002 and about 0.010 inches. The collar 60 may have a conical proximal surface 70 inclined at angle 72 to axis 74 of the rigid distal tip 26, and may include a distal surface 76 generally orthogonal to the axis 74. Angle 72 may be between about ten degrees and about 45 degrees, and more preferably between about ten degrees and about 30 degrees. Angle 84 of grooves 80 is preferably in the range of between about 0 and about 90 degrees. The distal surface 76 may be positioned proximate to the stop 49. The distal surface 76 of collar 60 may be positioned a distance 78 from a proximal end 79 of rigid distal tip 26. This configuration of the collar 60 enables the flexible transmission shaft 28 to be pushed onto the rigid distal tip 26 but prevent the flexible transmission shaft 28 from inadvertently being removed from the rigid distal tip 26 without application of significant force.

Figure 8:
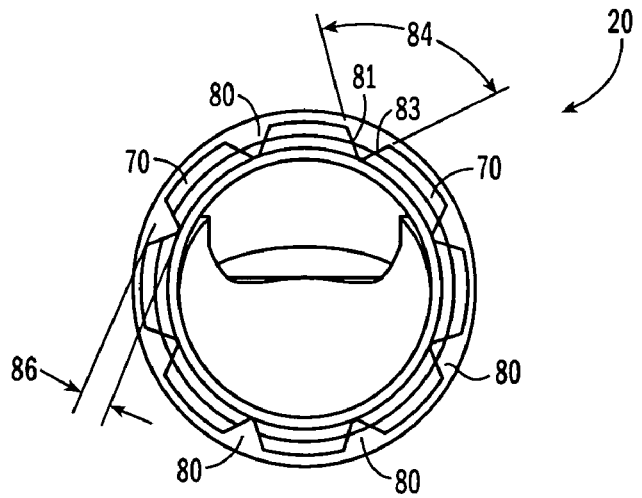
FIG. 8 is a distal axial view of the inner rigid distal tip shown in FIG. 6.
Figure 9:
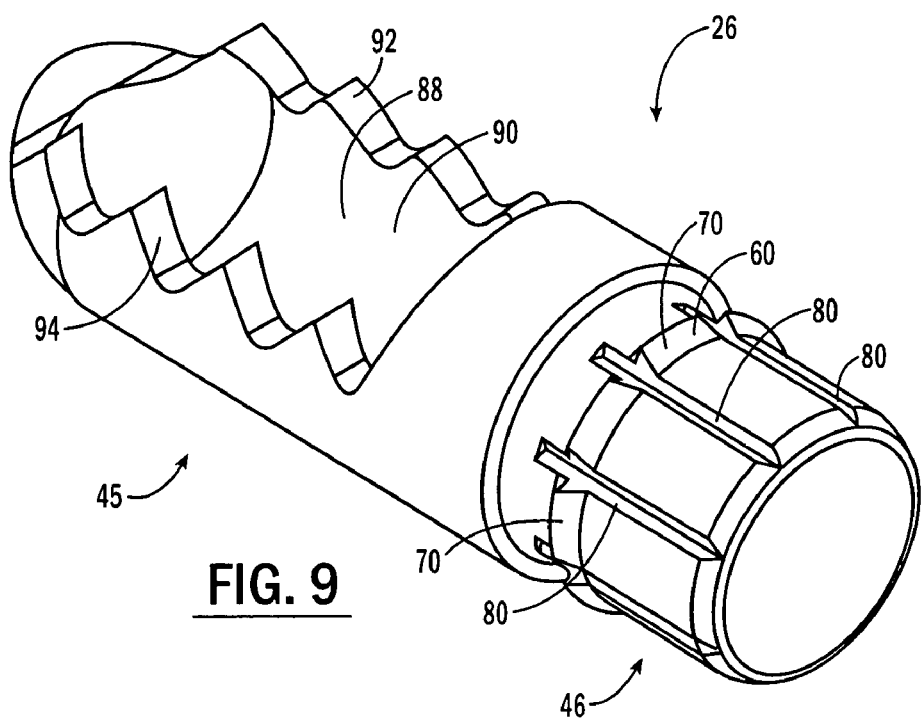
FIG. 9 is a perspective view of the inner rigid distal tip shown FIG. 6.

The connection system 1 may include one or more axial grooves 80. The grooves 80 may be positioned generally parallel to the longitudinal axis 74 or, in other embodiments, may be positioned at other angles relative to the longitudinal axis 74. The grooves 80 may extend a distance 82 from proximal end 79. In one embodiment, the distance 82 may be greater than the distance 78 such that the groove 80 terminates between the collar 60 and the stop 49. The grooves 80 may extend from the end 51. As shown in FIG. 8, grooves 80 may be formed from first and second sides 81, 83 that intersect with each other forming angle 84 and a depth 86. Distal portion 88 of rigid distal tip 26 may form a cutting window 90 with cutting edges 92 and 94. The distal portion 50 of the inner rigid proximal portion 24 of the drive system 14 may be identical in configuration to the proximal portion 46 of rigid distal tip 26 and may function in the same manner.

Figure 10:
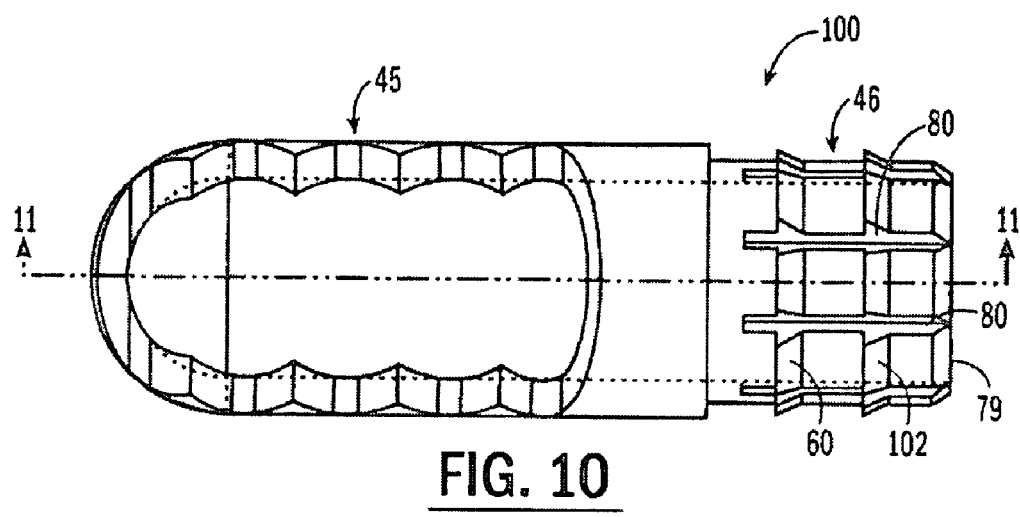
FIG. 10 is a top view of an alternate embodiment of the inner rigid distal tip.
Figure 11:
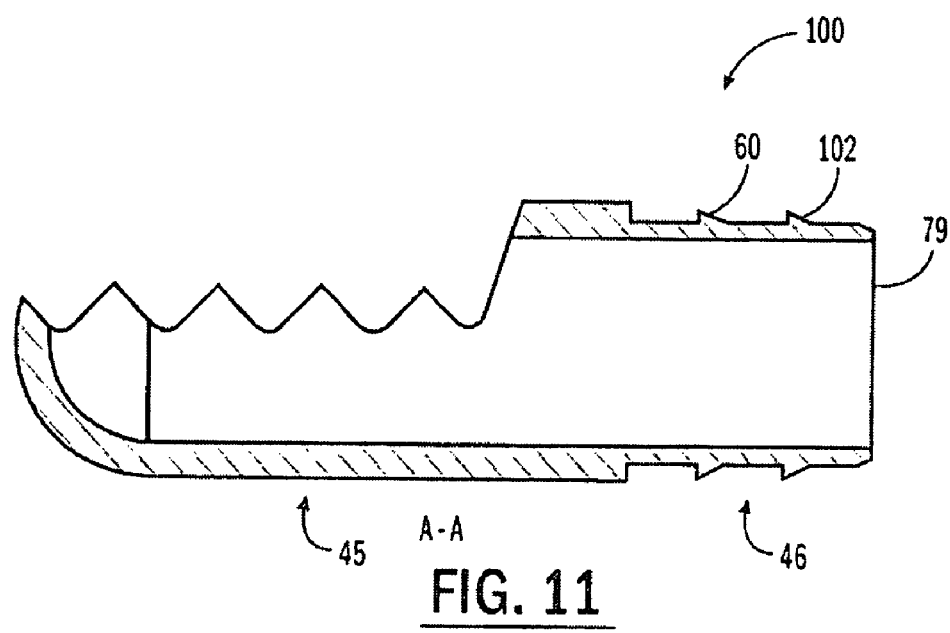
FIG. 11 is a cross-sectional view of the inner rigid distal tip shown in FIG. 10.
Figure 12:
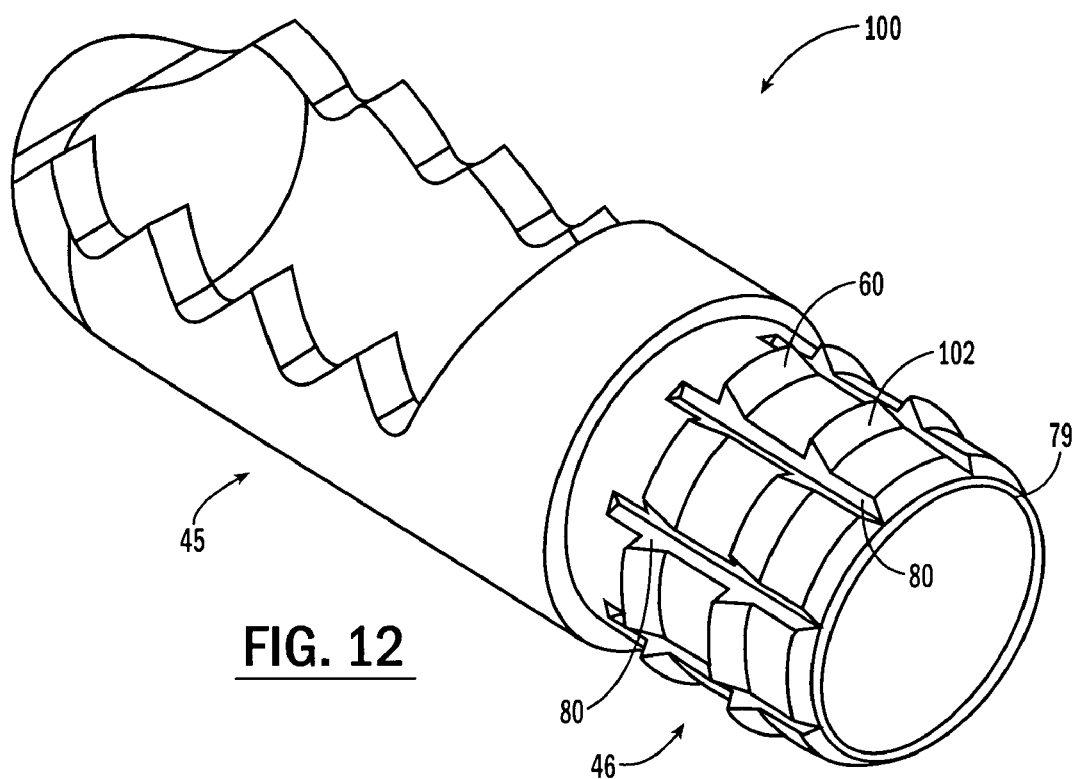
FIG. 12 is a perspective view of the inner rigid distal tip shown in FIG. 10.

In an alternate embodiment, as shown in FIGS. 10-12, the connection system 1 may include a plurality of collars 60. In one embodiment, the connection system 1 may include two collars 60 on the rigid distal tip 100. Other embodiments may have other numbers of collars 60. The collars 60 may penetrate into the wall of lumen 54 of flexible transmission shaft 28 to increase the holding power of the connection system 1 during use.

Figure 13:
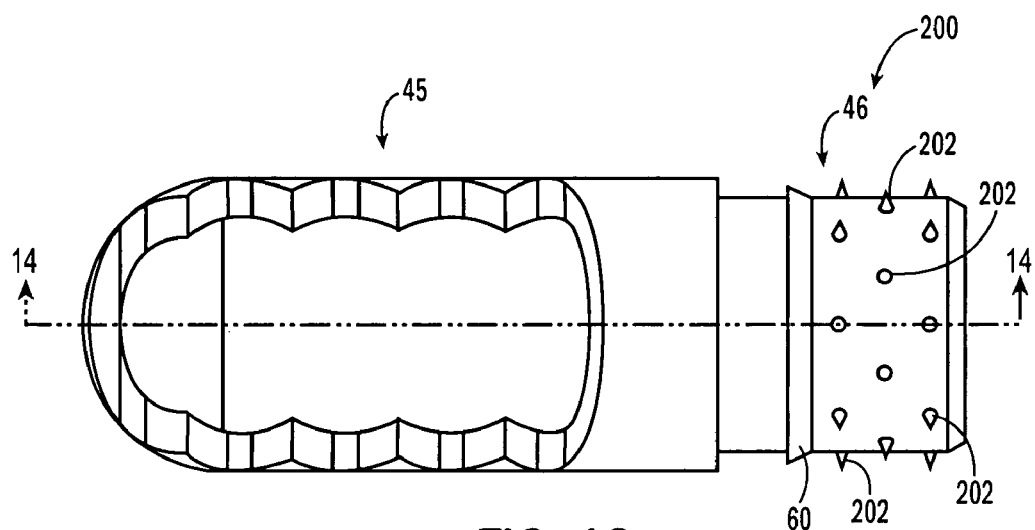
FIG. 13 is a top view of another alternative embodiment of the inner rigid distal tip.
Figure 14:
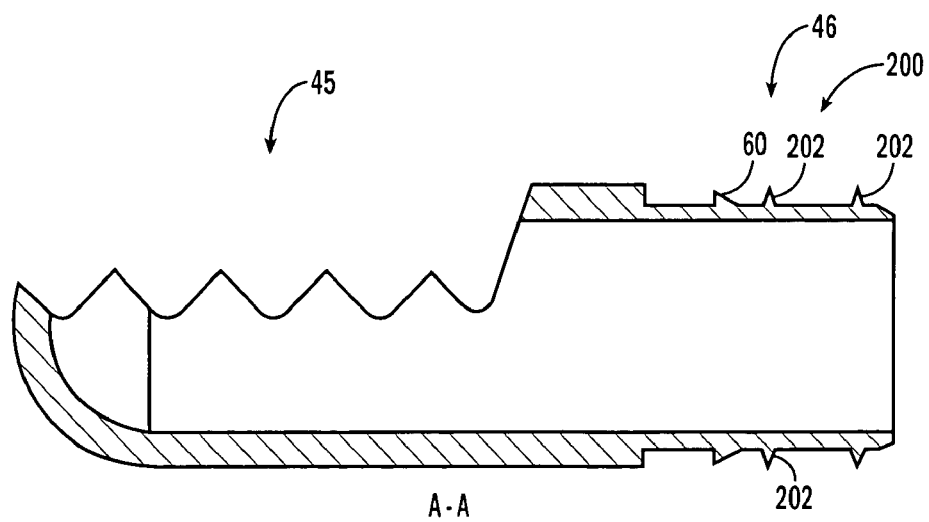
FIG. 14 is a cross-sectional view of the inner rigid distal tip shown in FIG. 13.
Figure 15:
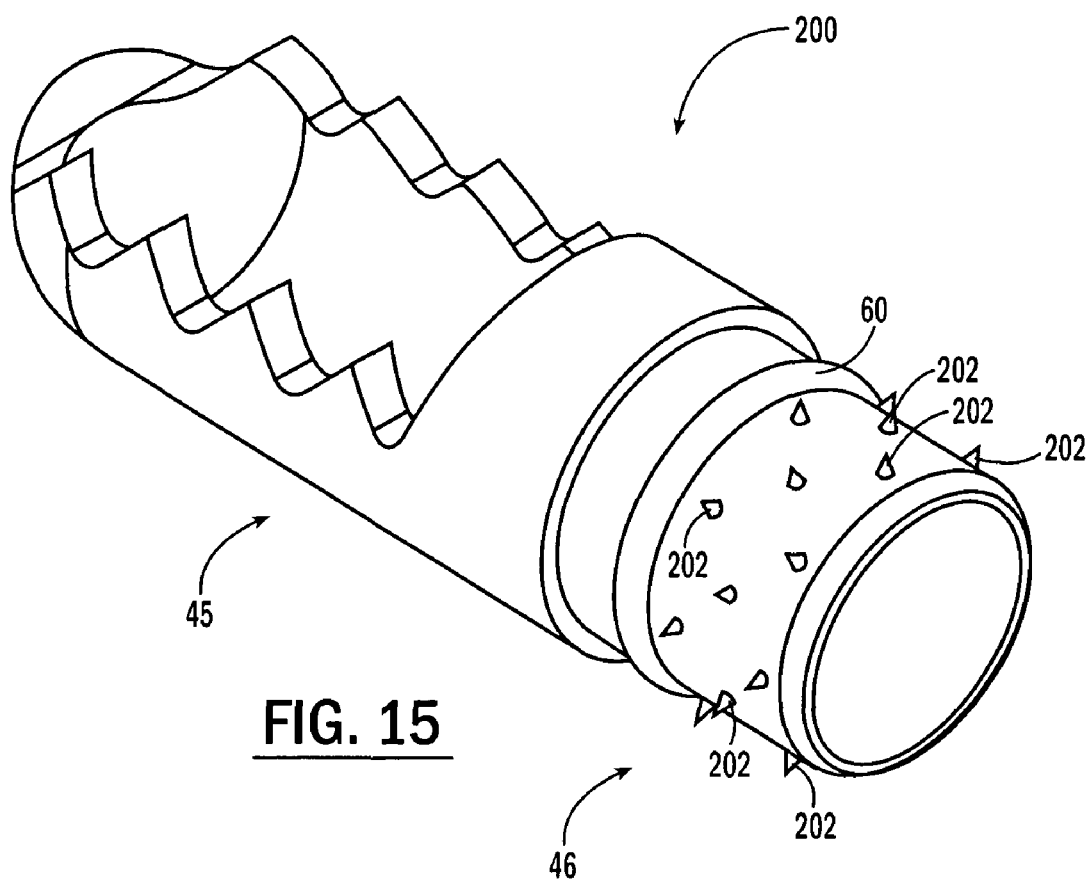
FIG. 15 is a perspective view of the inner rigid distal tip shown in FIG. 14.

FIGS. 13 through 15 depict another alternative embodiment having increased torsional strength. Rigid distal tip 200 may be identical to rigid distal tip 26 except that grooves 80 have been replaced by a plurality of projections 202. During use, projections 202 may penetrate the walls of lumen 54 of member 58 to transmit torque and provide the joint with additional tensile strength.

Figure 16:
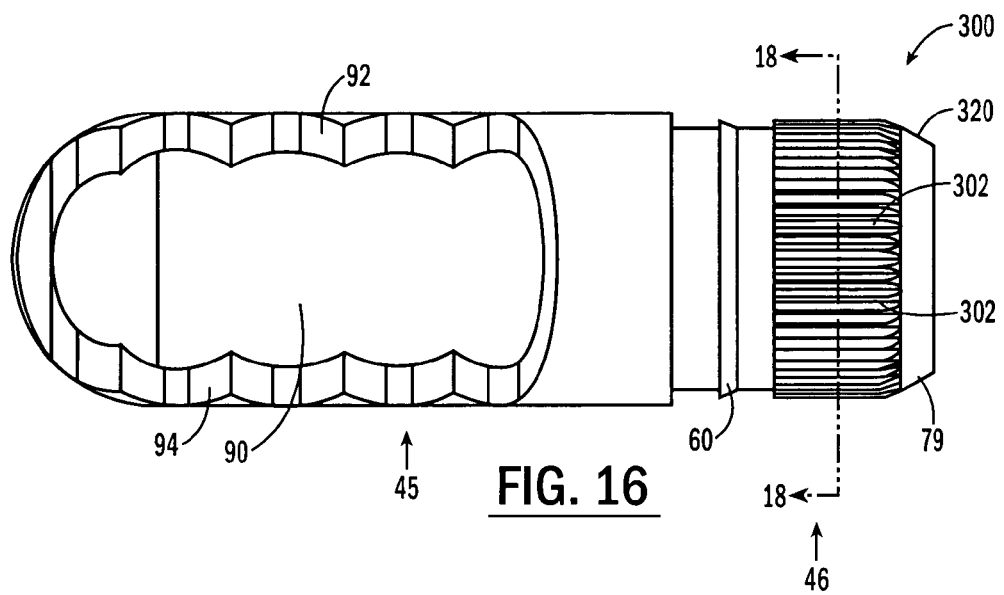
FIG. 16 is a top view of another alternative embodiment of the inner rigid distal tip.
Figure 17:
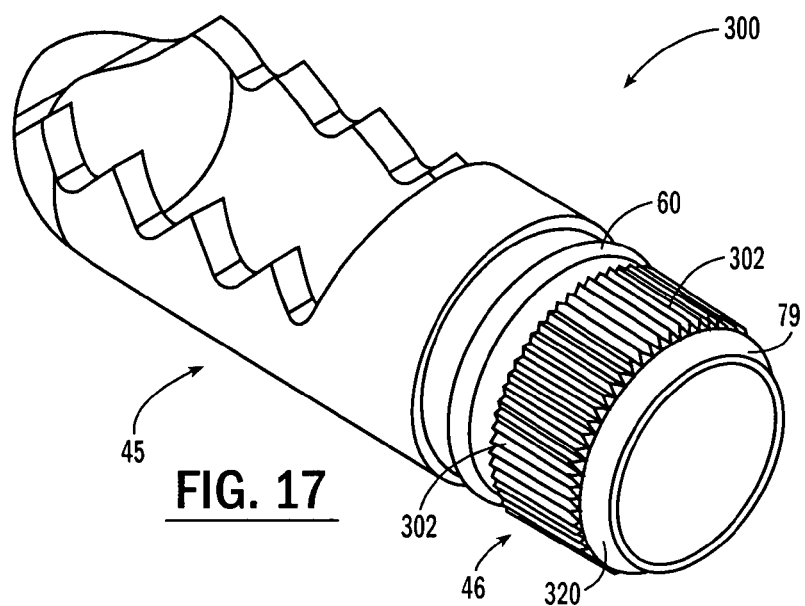
FIG. 17 is a perspective view of the inner rigid distal tip shown in FIG. 16.
Figure 18:
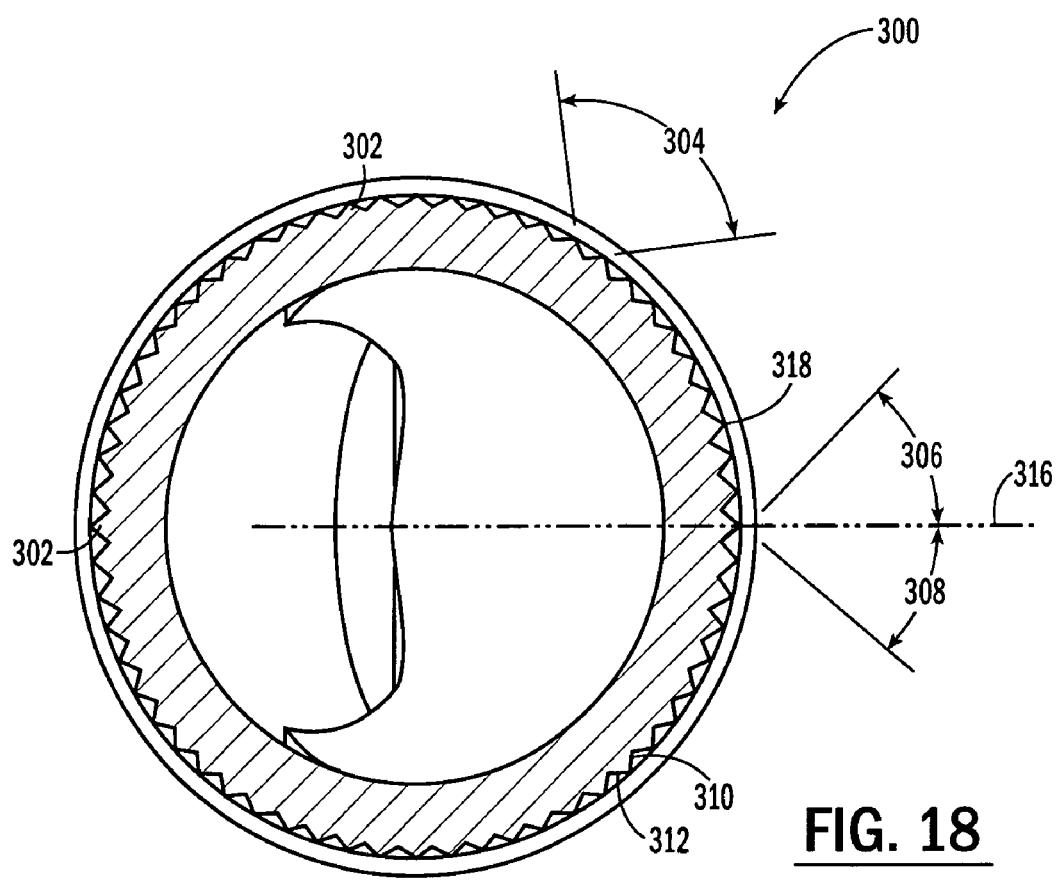
FIG. 18 is a cross-sectional view taken at line 18-18 in FIG. 16.

In yet another embodiment, as shown in FIGS. 16-18, rigid distal tip 300 may have a distal portion 45 identical to that of the previous embodiments, however proximal portion 46 may have a plurality of axial ribs 302 proximate to the collar 60. The ribs 302 may be positioned between the collar 60 and the end 51. The ribs 302 may have first surfaces 310 offset at angle 308 from radial line 316 and may include second surfaces 312 offset at angle 306 from radial line 316. In one embodiment, angles 306 and 308 may be approximately equal and may together form angle 304. First and second surfaces 310 and 312 may intersect to form edges 318. Proximal tapered portion 320 adjacent to proximal end 79 may allow proximal portion 46 to be inserted into lumen 54 of flexible transmission shaft 28. When positioned on flexible transmission shaft 28, ribs 302 may penetrate the wall of lumen 54 of flexible transmission shaft 28, thereby enabling the transmission of torque from flexible transmission shaft 28 to rigid distal tip 300. As with previous embodiments, collar 60 may penetrate the wall of lumen 54 to provide axial strength to the joint.

Figure 19:
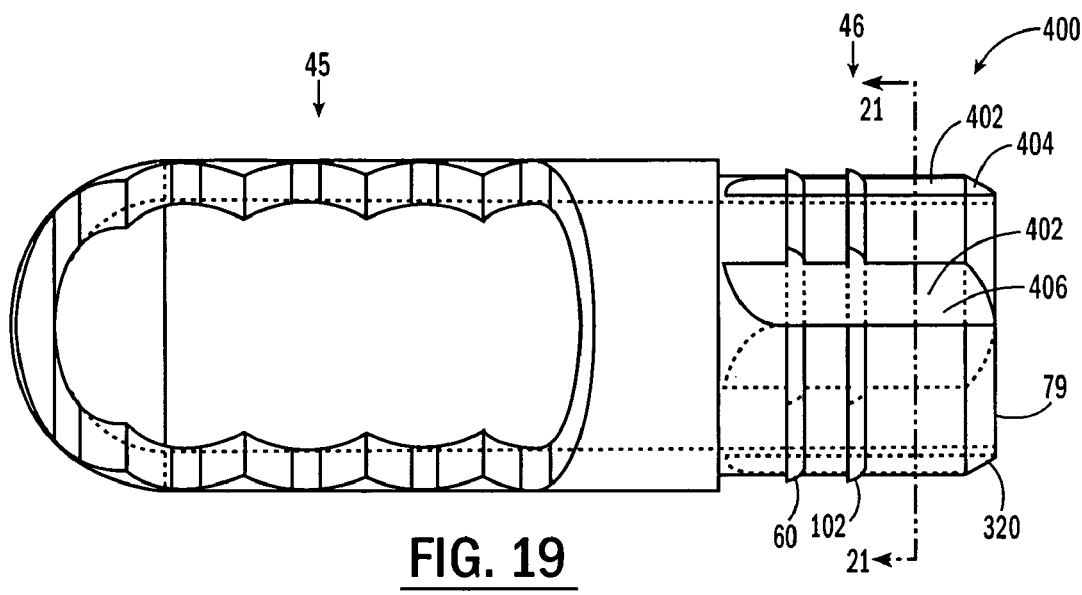
FIG. 19 is a top view of another embodiment of the inner rigid distal tip.
Figure 20:
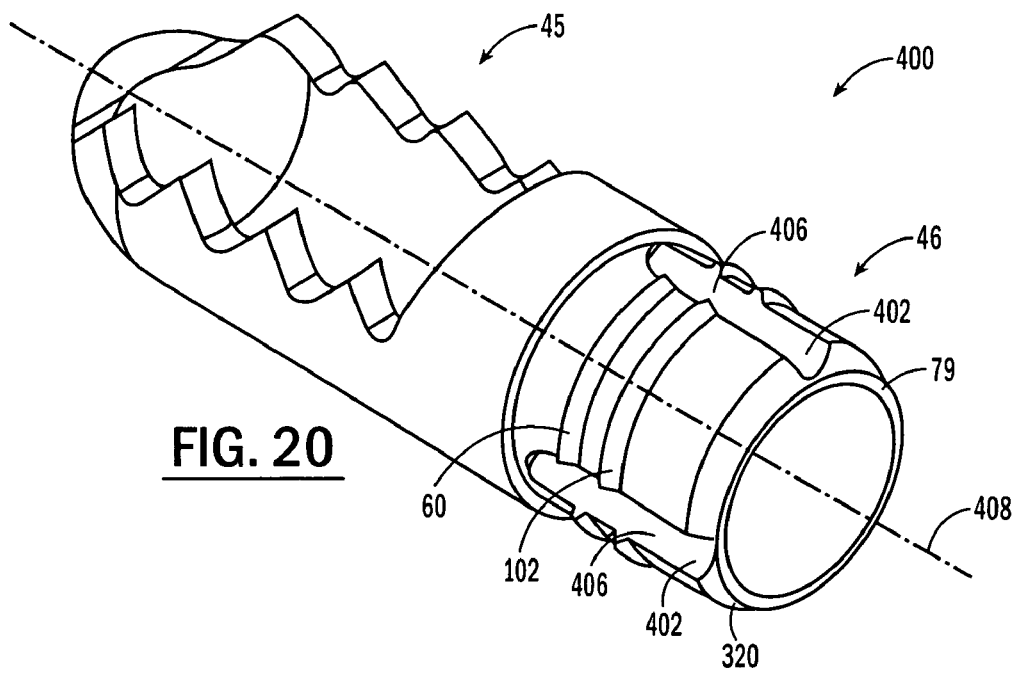
FIG. 20 is a perspective view of the inner rigid distal tip shown in FIG. 19.
Figure 21:
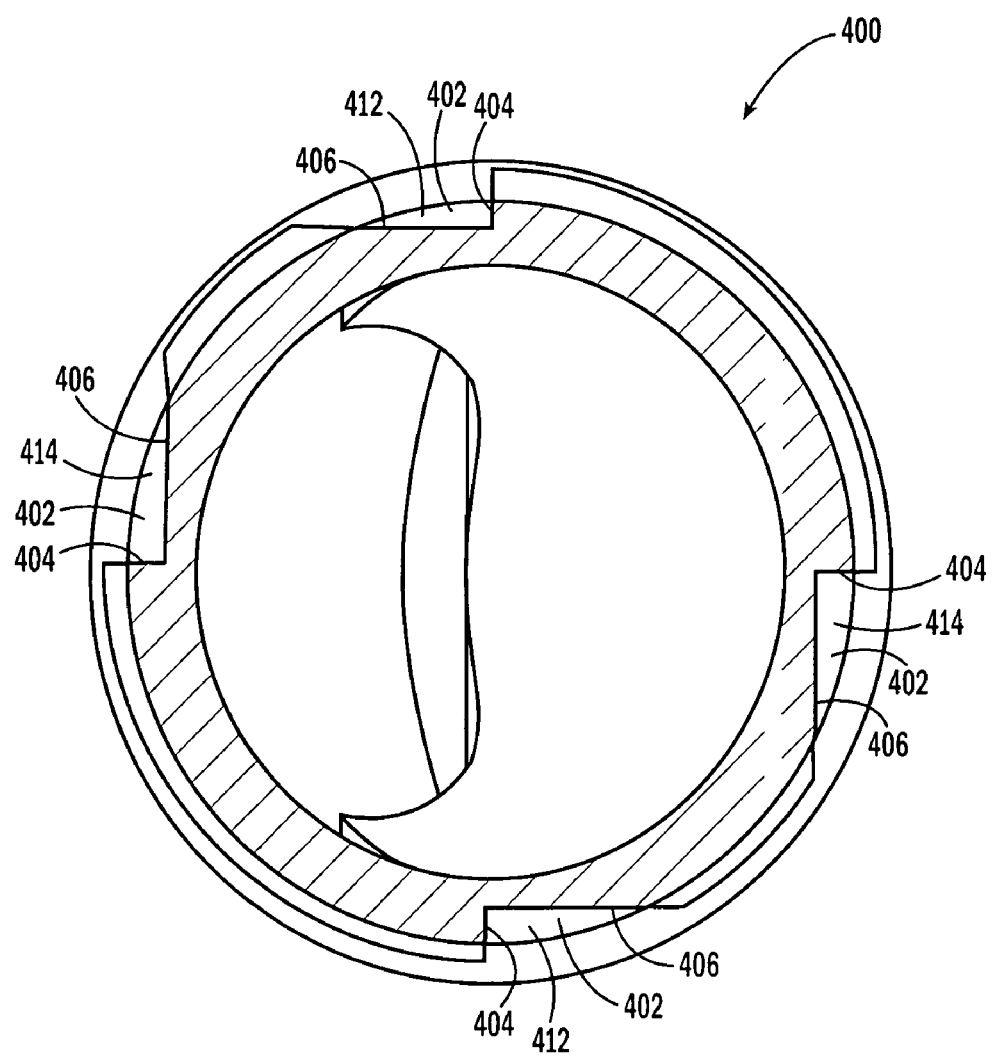
FIG. 21 is a cross-sectional view taken at line 21-21 in FIG. 19.
Figure 22:
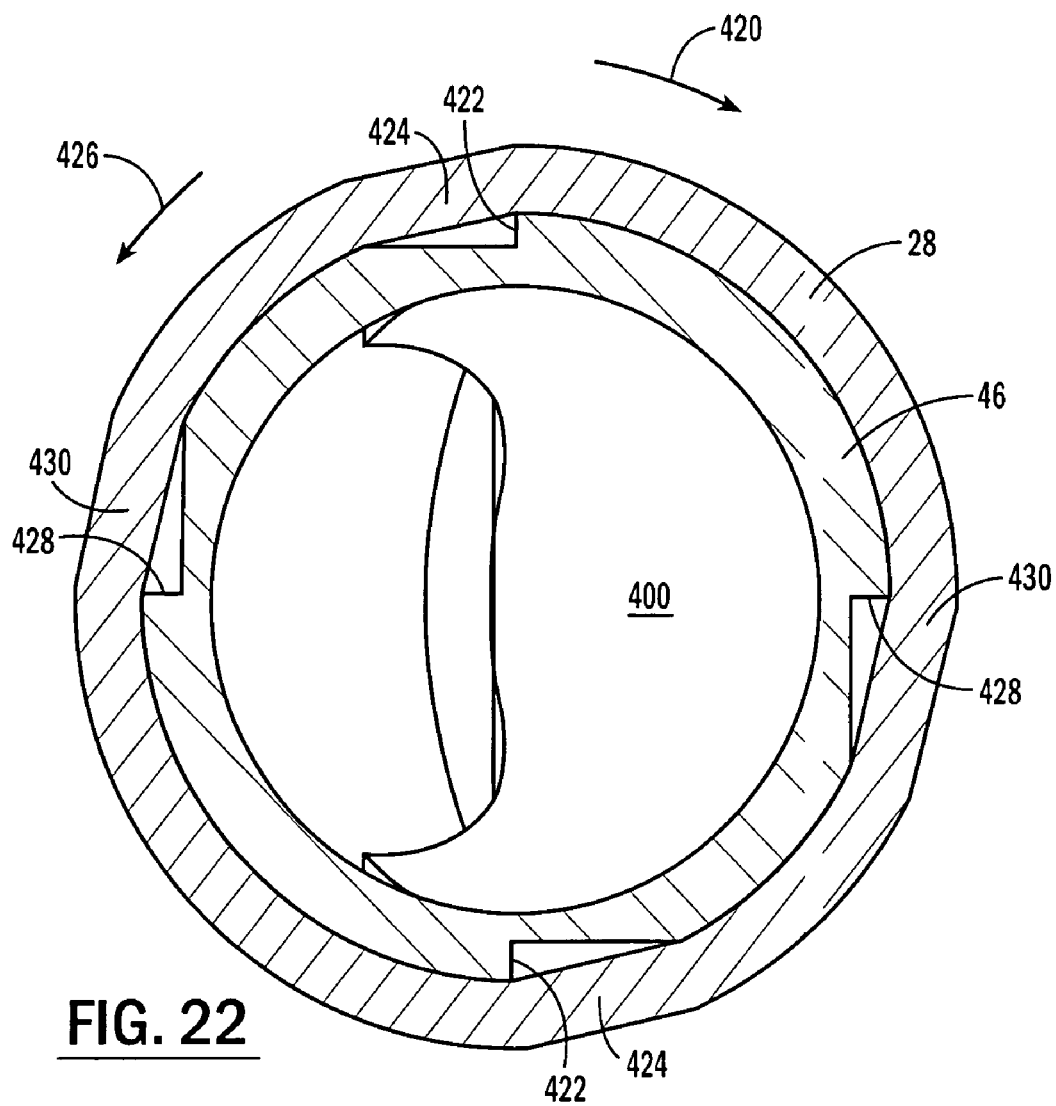
FIG. 22 is a cross-sectional view of the joint between the inner rigid distal tip of FIG. 19 and the flexible transition shaft.
Figure 23:
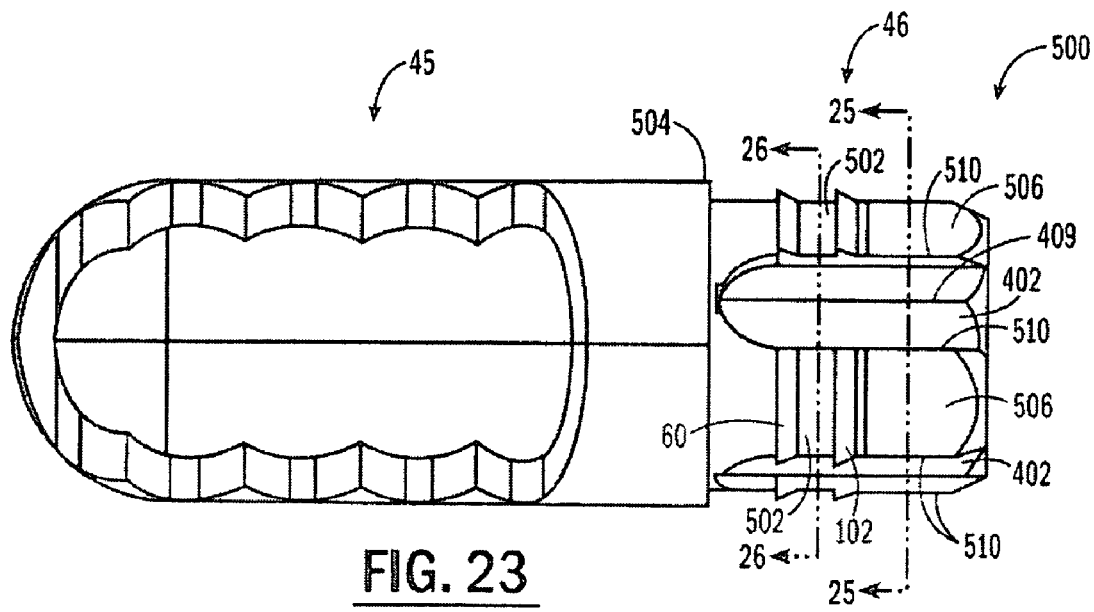
FIG. 23 is a top view of another embodiment of the inner rigid distal tip.
Figure 24:
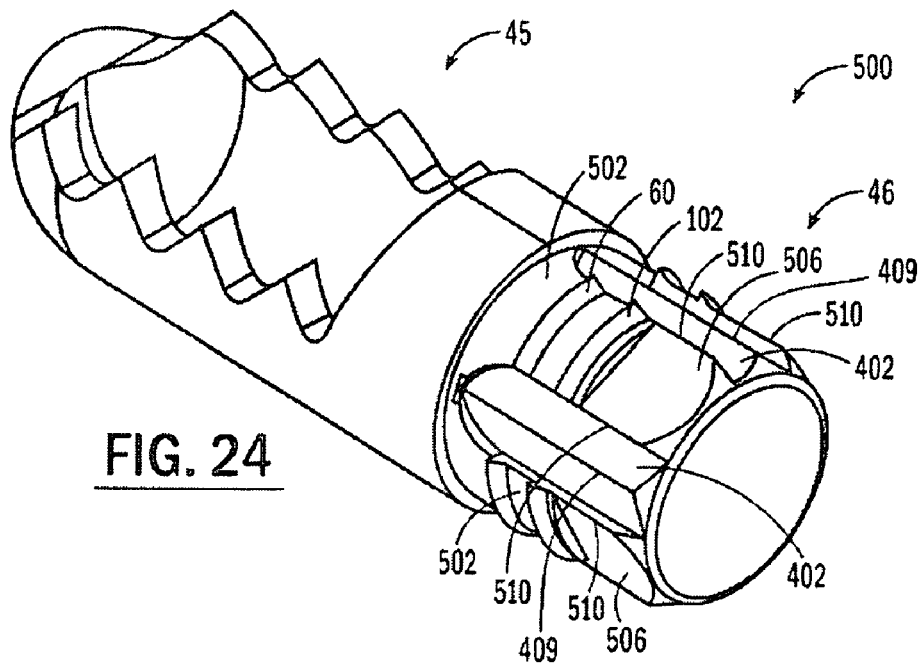
FIG. 24 is a perspective view of the inner rigid distal tip shown in FIG. 23.
Figure 25:
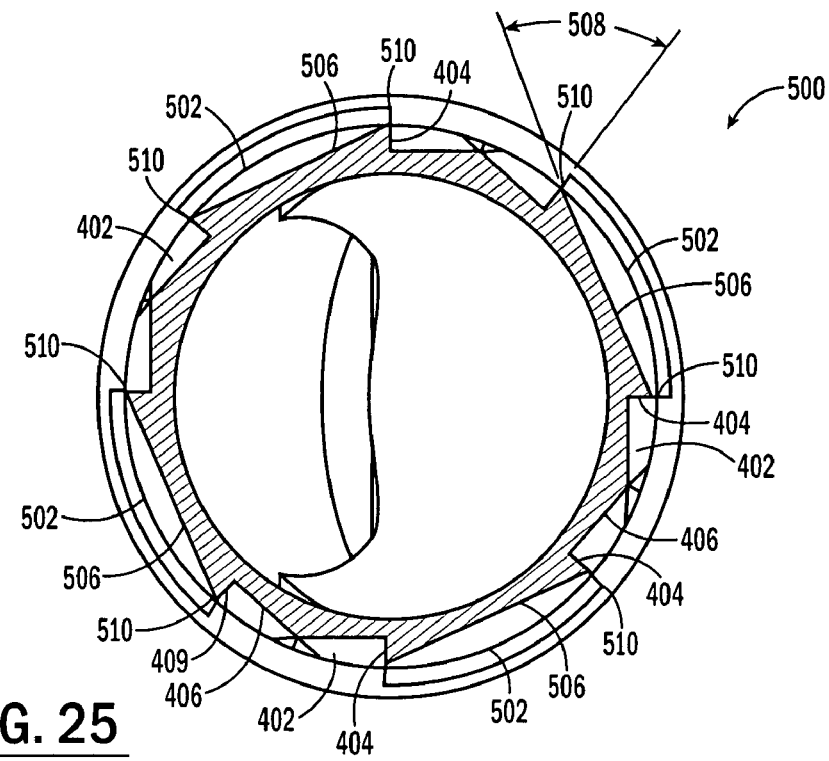
FIG. 25 is a cross-sectional view at line 25-25 in FIG. 23.

In another embodiment, as shown in FIGS. 19-21, rigid distal tip 400 may have a distal portion 45 and a proximal portion 46 having a first collar 60 and a second collar 102. Proximal portion 46 may also include a plurality of axial grooves 402 having first surfaces 404 and second surfaces 406. First surfaces 404 may extend radially outward, as shown in FIG. 21, and second surfaces 406 may be approximately orthogonal to first surfaces 404. As shown in FIG. 21, grooves 402 may be symmetric about line 408. Proximal tapered portion 320 adjacent to proximal end 79 may allow proximal portion 46 to be inserted into lumen 54 of flexible transmission shaft 28. As shown in FIG. 21, a depth of the groove 402 on a first side may be greater than a depth of the at least one groove on a second side. As shown in FIG. 22, when the flexible transmission shaft 28 is positioned on the rigid distal tip 400 by pressing of proximal portion 46 into lumen 54, portions of the flexible transmission shaft 28 bridging grooves 402 deform into the gaps formed by the grooves 402. When the joint formed is subjected to a torsional force in a first direction 420, first surfaces 422 penetrate into deformed material 424 of flexible transmission shaft 28. When a torsional force in a second direction 426 is applied to flexible transmission shaft 28, first surfaces 428 penetrate into deformed material 430 of flexible transmission shaft 28. Thus, the grooves 402 may be positioned such that the radially extending first surfaces 404 and second surfaces 406 extending therefrom may extend in clockwise and counter-clockwise directions.

Figure 26:
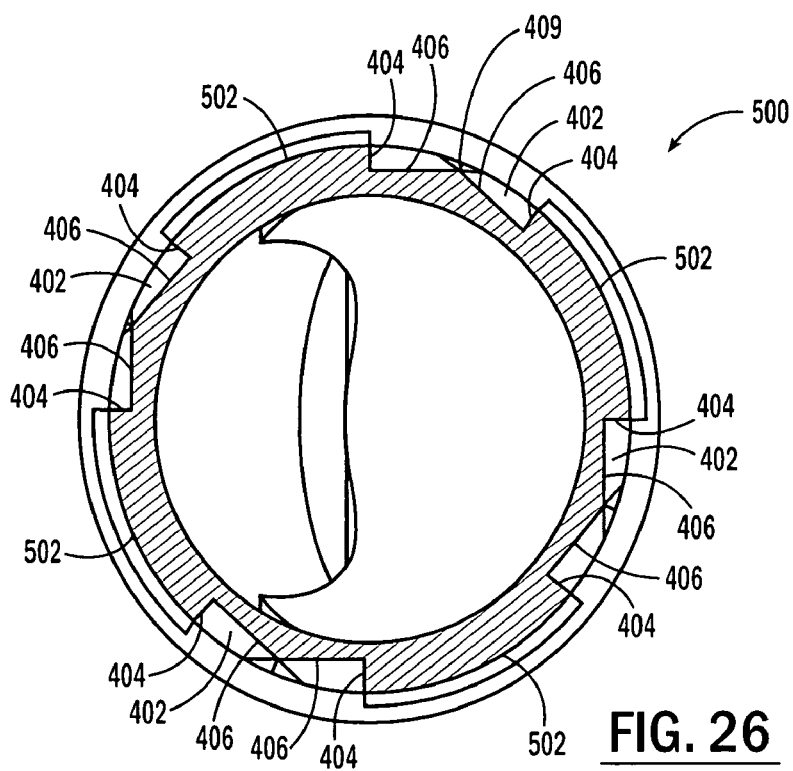
FIG. 26 is a cross-sectional view at line 26-26 in FIG. 23.

In yet another embodiment, as shown in FIGS. 23 through 26, rigid distal tip 500 may include a distal portion 45 identical to those of the previous embodiments. The rigid distal tip 500 may include a first collar 60 and a second collar 102. The rigid distal tip 500 may include a plurality of axial grooves 402 having first surfaces 404 and second surfaces 406. First surfaces 404 may extend radially, as shown in FIG. 26, and second surfaces 406 may be positioned generally orthogonal to first surfaces 404. Cylindrical surface portions 502 between grooves 402 extend from distal end 504 of proximal portion 406 to slightly proximal of second collar 102. Proximate to cylindrical surface portions 502, planar surfaces 506 may be formed between grooves 402 so that an acute angle 508 may be formed between first surfaces 404 and surfaces 506 at edges 510. Axial grooves 402 function in the same manner as in the previous embodiment. Because edges 510 are formed with an acute angle 508, forces formed between edges 510 and flexible transmission shaft 28 are high, thereby causing increased penetration of edges 510 into the flexible transmission shaft 28 upon assembly and when the joint between proximal portion 46 of rigid distal tip 500 and flexible transmission shaft 28 is subjected to a torsional force. The grooves 402 may have a center portion 409 with a depth that is less than a depth of the first surfaces 404.

The flexible transmission shaft 28 may be positioned on rigid distal tip 26 and the rigid proximal portion 24. In particular, the flexible transmission shaft 28 may be slide onto the receiver portion 47 until the flexible transmission shaft 28 contacts the stop 49. As previously discussed, the flexible transmission shaft 28 may form an interference fit when pushed onto the rigid distal tip 26 and the rigid proximal portion 24. The collar 60, and in some embodiments, collar 102, may retain the flexible transmission shaft 28 on the rigid distal tip 26 and the rigid proximal portion 24 when subjected to axial loads. The grooves 80 and 402 also work to transmit forces from the rigid proximal portion 24 to the flexible transmission shaft 28. In particular, the flexible transmission shaft 28 over the grooves 80 may deform slightly into the grooves 80, as previously discussed, thereby enabling side edges of the groove to dig into the flexible transmission shaft 28 to transmit torque from the drive transmission to the flexible transmission shaft 28 and from the flexible transmission shaft 28 to the rigid distal tip 26. In some embodiments, the projections 202 may protrude into the flexible transmission shaft 28 further facilitating the transmission of torque as described above. In another embodiment, the ribs 302 may protrude into the flexible transmission shaft 28 further facilitating the transmission of torque as described above.

When elongated distal portion 16 of inner drive assembly 12 is assembled, the strength of the assembly may be increased by heating the joints, thereby softening the flexible transmission shaft 28 so that the polymeric material deforms into axial grooves, and the collars 60 and 102 and projections 202 undergo maximum penetration. After pushing the proximal portion 46 into the distal end of the flexible transmission shaft 28, a compressive force may be applied to the exterior surface of the flexible transmission shaft 28 so as to increase deformation of the flexible transmission shaft 28 and penetration of various features of proximal portion 46 into flexible transmission shaft 28.

In use, the rotary shaver 10 may be removably attached to a suitable powered hand piece (not shown). The hub assembly 32 of the outer housing 30 may be attached to a chuck in the distal end of the handpiece (not shown), and the inner hub 18 may engage a drive mechanism in the handpiece so that when the handpiece is activated, the inner drive assembly 12 may rotate relative to the outer housing 30. The distal end of shaver 10 may be brought into close proximity to or contact the tissue to be resected. Suction may be applied by the handpiece via the aspiration passage 19 in the hub 18. Tissue may cut in the outer window 69 and may be sucked through the outer window into the lumen of the elongated distal assembly 16 to inner window 90 of rigid distal tip 26. The tissue may be cut by the inner window 90 rotating past the outer window 69 and cutting the tissue. The resected tissue may be aspirated from the site via the lumen of elongated distal assembly 16 and aspiration passage 19 to the handpiece where the tissue is passed to an external collection vessel. If tissue becomes lodged in inner distal assembly 16, the tissue may be removed by removing the shaver 10 from the handpiece, removing the inner drive assembly 12 from the outer housing 30, and then inserting a wire or other elongated device into the lumen to push the tissue from the elongated distal assembly 16.

During use, the edges of grooves 80 on the proximal portion 46 of rigid distal tip 26 and on distal portion 50 of proximal portion 24 of the drive system 14 may cause the material of flexible transmission shaft 28 to deform into grooves 80 so as to transmit torque via flexible transmission shaft 28 to rigid distal tip 26. Collar 60 on rigid distal tip 26 and collar 60 on distal portion 50 of proximal portion 24 may embed into flexible transmission shaft 28 so that the assembly does not fail during removal of the inner drive assembly for de-clogging.

The foregoing is provided for purposes of illustrating, explaining, and describing embodiments of this invention. Modifications and adaptations to these embodiments will be apparent to those skilled in the art and may be made without departing from the scope or spirit of this invention.

We claim:
1. A rotary shaver, comprising:
 a rigid distal tip having a plurality of teeth positioned proximate to a distal opening for cutting tissue, an opening at a proximal end of the rigid distal tip, and a flexible shaft connection device at the proximal end;
 a rigid drive member having a drive attachment device at one end and a flexible shaft connection device at another end;
 a flexible transmission shaft coupled to the rigid distal tip at the flexible shaft connection device of the rigid distal tip and extending from the rigid distal tip to the rigid drive member, wherein the flexible transmission shaft is attached to the flexible shaft connection device of the rigid drive member;
 wherein at least one of the flexible shaft connection device of the rigid distal tip and of the rigid drive member comprises at least one collar protruding radially outward from an outer surface and positioned between a stop and an end of the flexible shaft connection device to attach the flexible transmission shaft;
 wherein the flexible transmission shaft is positioned over the at least one collar and abuts the stop;
 wherein the flexible transmission shaft includes an inner, smooth, tubular surface that the at least one collar contacts;
 at least one linear groove positioned in the outer surface and positioned generally along a longitudinal axis of one of the flexible shaft connection device of the rigid distal tip and of the rigid drive member from which the at least one collar extends; and wherein a depth of the at least one linear groove on a first side of the at least one linear groove is greater than a depth of the at least one linear groove on a second side of the at least one linear groove.

2. The rotary shaver of claim 1, wherein the at least one collar is positioned generally orthogonal to a longitudinal axis of one of the flexible shaft connection device of the rigid distal tip and of the rigid drive member.

3. The rotary shaver of claim 1, wherein the at least one linear groove comprises a plurality of linear grooves extending generally along a longitudinal axis of one of the flexible shaft connection device of the rigid distal tip and of the rigid drive member from which the at least one collar extends.

4. The rotary shaver of claim 3, wherein the at least one linear groove comprises first and second sides extending from the outer surface and intersecting one another.

5. The rotary shaver of claim 3, wherein the at least one linear groove extends from an end of the flexible shaft connection device toward the stop and terminates between the at least one collar and the stop.

6. The rotary shaver of claim 5, further comprising a second collar protruding from the outer surface and positioned between the at least one collar and the end of the flexible shaft connection device.

7. The rotary shaver of claim 1, wherein the end of the rigid drive member is tapered to facilitate attachment of the flexible transmission shaft.

8. A curved rotary shaver, comprising:
an elongated, tubular outer housing having an opening at one end and a cutting window at another opposite end, wherein a longitudinal axis of a portion of the outer housing proximate to the cutting window is positioned at an acute angle relative to remaining portions of the outer housing;
a support housing attached to the elongated, tubular outer housing proximate to the opening;
a rotatable inner cutting member, comprising: a rigid distal tip having a plurality of teeth positioned proximate to a distal opening for cutting tissue, an opening at a proximal end of the rigid distal tip, and a flexible shaft connection device at the proximal end;
a rigid drive member having a drive attachment device at one end and a flexible shaft connection device at another end;
a flexible transmission shaft coupled to the rigid distal tip at the flexible shaft connection device of the rigid distal tip and extending from the rigid distal tip to the rigid drive member, wherein the flexible transmission shaft is attached to the flexible shaft connection device of the rigid drive member;
wherein at least one of the flexible shaft connection device of the rigid distal tip and of the rigid drive member comprises at least one collar protruding radially outward from an outer surface and positioned between a stop and an end of the flexible shaft connection device to attach the flexible transmission shaft;
wherein the flexible transmission shaft is positioned over the at least one collar and abuts the stop;
wherein the flexible transmission shaft includes an inner, smooth, tubular surface that which the at least one collar contacts;
a plurality of linear grooves positioned in the outer surface and positioned generally along a longitudinal axis of one of the flexible shaft connection device of the rigid distal tip and of the rigid drive member from which the at least one collar extends; and wherein a depth of at least one linear groove on a first side of the at least one linear groove is greater than a depth of the at least one linear groove on a second side of the at least one linear groove.

9. The rotary shaver of claim 8, wherein the at least one collar is positioned generally orthogonal to a longitudinal axis of one of the flexible shaft connection device of the rigid distal tip and of the rigid drive member.

10. The rotary shaver of claim 8, wherein the plurality of linear grooves extend from an end of the flexible shaft connection device toward the stop and terminate between the at least one collar and the stop.

11. The rotary shaver of claim 10, further comprising a second collar protruding from the outer surface and positioned between the at least one collar and the end of the flexible shaft connection device.

12. The rotary shaver of claim 8, wherein the end of the rigid drive member is tapered to facilitate attachment of the flexible transmission shaft.

13. A curved rotary shaver, comprising:
an elongated, tubular outer housing having an opening at one end and a cutting window at another opposite end, wherein a longitudinal axis of a portion of the outer housing proximate to the cutting window is positioned at an acute angle relative to remaining portions of the outer housing;
a support housing attached to the elongated, tubular outer housing proximate to the opening;
a rotatable inner cutting member, comprising: a rigid distal tip having a plurality of teeth positioned proximate to a distal opening for cutting tissue, an opening at a proximal end of the rigid distal tip, and a flexible shaft connection device at the proximal end;
a rigid drive member having a drive attachment device at one end and a flexible shaft connection device at another end;
a flexible transmission shaft coupled to the rigid distal tip at the flexible shaft connection device of the rigid distal tip and extending from the rigid distal tip to the rigid drive member, wherein the flexible transmission shaft is attached to the flexible shaft connection device of the rigid drive member;
wherein at least one of the flexible shaft connection device of the rigid distal tip and of the rigid drive member comprises at least one collar protruding radially outward from an outer surface and positioned between a stop and an end of the flexible shaft connection device to attach the flexible transmission shaft;
wherein the flexible transmission shaft is positioned over the at least one collar and abuts the stop;
wherein the flexible transmission shaft includes an inner, smooth, tubular surface that which the at least one collar contacts;
a plurality of linear grooves positioned in the outer surface and positioned generally along a longitudinal axis of one of the flexible shaft connection device of the rigid distal tip and of the rigid drive member from which the at least one collar extends; and
wherein a depth of at least one linear groove along a center line of the at least one linear groove is less than a depth of the linear groove at first and second sides of the at least one linear groove thereby forming torque transmitting connection device capable of transmitting torque when the flexible shaft is rotated in both clockwise and counterclockwise directions.

14. The rotary shaver of claim 13, wherein the at least one collar is positioned generally orthogonal to a longitudinal axis of one of the flexible shaft connection device of the rigid distal tip and of the rigid drive member.

15. The rotary shaver of claim 13, wherein the plurality of linear grooves extend from an end of the flexible shaft connection device toward the stop and terminate between the at least one collar and the stop.

16. The rotary shaver of claim 15, further comprising a second collar protruding from the outer surface and positioned between the at least one collar and the end of the flexible shaft connection device.

17. The rotary shaver of claim 13, wherein the end of the rigid drive member is tapered to facilitate attachment of the flexible transmission shaft.

18. A rotary shaver, comprising:
- a rigid distal tip having a plurality of teeth positioned proximate to a distal opening for cutting tissue, an opening at a proximal end of the rigid distal tip, and a flexible shaft connection device at the proximal end;
- a rigid drive member having a drive attachment device at one end and a flexible shaft connection device at another end;
- a flexible transmission shaft coupled to the rigid distal tip at the flexible shaft connection device of the rigid distal tip and extending from the rigid distal tip to the rigid drive member, wherein the flexible transmission shaft is attached to the flexible shaft connection device of the rigid drive member;
- wherein at least one of the flexible shaft connection device of the rigid distal tip and of the rigid drive member comprises at least one collar protruding radially outward from an outer surface and positioned between a stop and an end of the flexible shaft connection device to attach the flexible transmission shaft;
- wherein the flexible transmission shaft is positioned over the at least one collar and abuts the stop;
- wherein the flexible transmission shaft includes an inner, smooth, tubular surface that the at least one collar contacts;
- at least one linear groove positioned in the outer surface and positioned generally along a longitudinal axis of one of the flexible shaft connection device of the rigid distal tip and of the rigid drive member from which the at least one collar extends; and
- wherein a depth of the at least one linear groove along a center line of the linear groove is less than a depth of the at least one linear groove at first and second sides of the at least one linear groove thereby forming torque transmitting connection device capable of transmitting torque when the flexible shaft is rotated in both clockwise and counterclockwise directions.

19. The rotary shaver of claim 18, wherein the at least one collar is positioned generally orthogonal to a longitudinal axis of one of the flexible shaft connection device of the rigid distal tip and of the rigid drive member.

20. The rotary shaver of claim 18, wherein the at least one linear groove comprises a plurality of linear grooves extending generally along a longitudinal axis of one of the flexible shaft connection device of the rigid distal tip and of the rigid drive member from which the at least one collar extends.

21. The rotary shaver of claim 20, wherein the at least one linear groove comprises first and second sides extending from the outer surface and intersecting one another.

22. The rotary shaver of claim 20, wherein the at least one linear groove extends from an end of the flexible shaft connection device toward the stop and terminates between the at least one collar and the stop.

23. The rotary shaver of claim 22, further comprising a second collar protruding from the outer surface and positioned between the at least one collar and the end of the flexible shaft connection device.

24. The rotary shaver of claim 18, wherein the end of the rigid drive member is tapered to facilitate attachment of the flexible transmission shaft.

* * * * *